United States Patent [19]

Yaralian

[11] 4,455,304

[45] Jun. 19, 1984

[54] COMPOSITION FOR REPELLING BIRDS

[76] Inventor: Kourken Yaralian, 5336 E. Easterby Dr., Fresno, Calif. 93727

[21] Appl. No.: 369,984

[22] Filed: Apr. 19, 1982

[51] Int. Cl.$^3$ .............................................. A61K 35/78
[52] U.S. Cl. .................................................... 424/195
[58] Field of Search .................. 424/195, 30, DIG. 10

[56] References Cited

U.S. PATENT DOCUMENTS

| 631,738 | 8/1899 | Dowie et al. | 424/195 |
| 779,634 | 1/1905 | Allen | 424/161 |
| 3,051,617 | 8/1962 | Mann | 424/195 |

FOREIGN PATENT DOCUMENTS 2222025 10/1974 France .

OTHER PUBLICATIONS

Helen F. Su, "Insecticidal Properties of Black Pepper to Rice Weevils and Cowpea Weevils," *Journal of Economic Entomology*, Feb. 1977, pp. 18–21.
Pest Control, "Animal Repellents", pp. 18–19, Dec. 1949.

*Primary Examiner*—Albert T. Meyers
*Assistant Examiner*—John W. Rollins
*Attorney, Agent, or Firm*—Huebner & Worrel

[57] ABSTRACT

A composition for repelling birds, the composition having as active ingredients finely divided dried pepper from pungent fruits of plants of the genus Capsicum and finely divided dried garlic and typically being diluted by inert, finely divided mineral material or water for application to the earth surface or to growing plants to repel birds given to eating seeds, plants, vegetables, and fruits.

9 Claims, No Drawings

COMPOSITION FOR REPELLING BIRDS

BACKGROUND OF THE INVENTION

1. Field of the Invention

The present invention relates to a composition for repelling birds and more particularly to such a composition in which the active ingredients are natural, organic plant derivatives and which is applied in the field to reduce or eliminate bird damage to plants and their fruits.

2. Description of the Prior Art

Damage to seeds, growing vegetables, and fruits by birds which eat the same is a serious problem to commercial growers. A particularly serious problem occurs with birds, such as the horned lark (Eremophila alpestris), which attack seeds or plants as they first emerge from the earth thereby effectively preventing survival or growth of the plants before any benefit is obtained therefrom.

It is, therefore, highly desirable to provide a repellant useful for application in the field to repel such birds, the repellant having no adverse effects on the environment or on consumers of fruits or vegetables from plants treated with the repellant. Although scarecrows, frightening sounds, and certain materials used in food flavoring have been used to repel birds, they are either insufficiently effective or are uneconomical for use in the field with commercially grown vegetables and fruits.

PRIOR ART STATEMENT

Characterizing the closest prior art of which the applicant is aware and in conformance with 37 C.F.R. §1.97 and §1.98, attention is invited to the following publication and patents, copies of which are enclosed together with Form PTO-1449.

Publication:

Helen C. F. Su, "Insecticidal Properties of Black Pepper to Rice Weevils and Cowpea Weevils," *Journal of Economic Entomology*, February 1977, pp. 18–21.

| U.S. Pat. Nos.: | | |
|---|---|---|
| 631,738 | Dowie et al. | Aug. 22, 1899 |
| 779,634 | Allen | Jan. 10, 1905 |
| 3,051,617 | Mann | Aug. 28, 1962 |

The Dowie U.S. Pat. No. 631,738; the Allen U.S. Pat. No. 779,634; and the publication, "Insecticidal Properties of Black Pepper," are believed relevant in their disclosure of the use of various kinds of pepper derivatives to repel pests. The Dowie patent discloses the use of chili pepper to repel rodents and the Allen patent discloses the use of cayenne pepper for the same purpose. The publication discloses the toxicity of black pepper, which is not derived from plants of the genus Capsicum, and black pepper derivatives to certain insects. The patent to Mann is believed relevant in its disclosure of the use of the flavoring material, anise, to repel birds.

SUMMARY OF THE INVENTION

It is an object of the subject invention to provide an improved composition for repelling birds.

Another object is to provide such a composition which is useful for application in the field to the earth surface and to growing crops to repel birds.

Another object is to provide such a composition which has, as the active ingredients, only natural organic substances.

Another object is to provide such a composition which is not dangerous to human consumers of fruits and vegetables from plants treated with the composition and which has no significant adverse environmental effects.

Another object is to provide such a composition which, although effective in preventing the eating by birds of crops growing in the field, does not effect the eating qualities of such crops.

Another object is to provide such a composition having the foregoing, and other objects and advantages which is characterized by the synergistic effect of cayenne pepper and garlic used together to repel birds and which is economical and safe to apply and is fully effective in carrying out its intended purposes.

DESCRIPTION OF EXEMPLARY EMBODIMENTS AND MANNER OF APPLICATION

A composition for repelling birds and other agricultural pests and embodying the principles of the present invention has as the active ingredients a derivative of garlic (*allium satiuum L.*) together with a derivative of cayenne pepper, a pungent pepper fruit borne by plants of the genus Capsicum. These derivatives, when used together in forms and in proportions shortly to be set forth, have a synergistic effect in repelling such pests. As a result, a composition embodying the principles of the present invention and having a predetermined combined weight of these two derivatives is substantially more effective than the use of an equal weight of one or the other, but not both, such derivatives.

Typically, the garlic derivative is finely divided, dried garlic bulbs. This derivative is commonly known as "garlic powder" and is commercially available as a flavoring. The pepper derivative is finely divided, dried cayenne pepper. Pepper derived from this genus is to be distinguished from pepper derived from plants of the genus Piper and commonly sold as "black pepper" or "white pepper" which are not suitable for use in the subject composition. Cayenne pepper is commercially available as a spice. These fruits of plants of the genus Capsicum vary substantially in pungency from mild to highly pungent. However, only those Capsicum pepper fruits which are highly pungent are effective in the practice of the present invention. More particularly, only such fruits which provide a finely divided dried pepper product having a pungency of 25,000 to 60,000 Scoville Heat Units are effective in practicing the present invention. Scoville Units are a measure of pungency of spices, well known to those in the spice trade, and are determined by a procedure set forth in a publication of the American Spice Trade Association, *Official Analytical Methods*, (1968) 2nd Edition, Method 21.0.

Examples

Preferred compositions for practicing the subject invention include food grade garlic powder and cayenne pepper well mixed in any of the following proportions by weight:

| Garlic Powder | Cayenne Pepper | Percent ratio by weight, garlic/cayenne |
|---|---|---|
| Example I | | |

| Cayenne Pepper | Garlic Powder | Percent ratio by weight, cayenne/garlic |
|---|---|---|
| 1 part | ¾ Parts to 1 part Example II | 57/43 to 50/50 |
| 2 parts | 1½ parts to 1 part Example III | 57/43 to 67/33 |
| 3 parts | 2 parts to 1 part Example IV | 60/40 to 75/25 |
| 4 parts | 3 parts to 1 part Example V | 57/43 to 80/20 |
| 5 parts | 4 parts to 1 part | 56/44 to 83/17 |
| | Example VI | |
| 1 part | 1 part Example VII | 50/50 |
| 2 parts | 1 part Example VIII | 33/67 |
| 3 parts | 2 parts to 1 part Example IX | 40/60 to 25/75 |
| 4 parts | 3 parts to 1 part Example X | 43/57 to 20/80 |
| 5 parts | 2 parts to 1 part | 29/71 to 17/83 |

Thus, it will be seen that from 1 to 5 parts cayenne pepper should be used with from 5 to 1 parts garlic, or expressed differently, each of these two ingredients should be used in a range of from 83% to 17% of the combined weights of the two ingredients. The garlic powder and the cayenne pepper may be in any dried and finely divided form, including the degrees of fineness commonly described by the terms "powdered," "comminuted," "granulated," or "crushed."

The listed compositions can be applied as mixed or the compositions may be diluted for application with diluent which is preferably inert. When it is desired to apply the composition in dry form, the diluent is finely divided inert mineral material, such as dolomite, talc, or phosphate rock, the desired ratio of dilution depending upon the expected pest infestation. For dry application of the compositions, from one to fifteen parts by weight of the mineral material in powdered form is, preferably, utilized per one part by weight of the garlic powder and cayenne pepper mixture. When it is desired to apply the composition in a liquid carrier, one part by weight of the mixture is dispersed in from about 40 to about 400 parts by weight of an aqueous medium, these proportions corresponding to about one pound (0.45 kilogram) of the garlic powder and cayenne pepper mixture to about 5 to about 50 gallons (about 19 to 190 liters) of water.

To repel birds which are given to eating unsprouted or newly sprouted seeds, the listed compositions are usually applied without dilution in any suitable manner, as by a granular applicator, on or adjacent to the seeds and/or sprouts of lettuce plants, melon plants, or other vegetable and fruit plants. The compositions, when applied in undiluted form for this purpose, are applied at a rate of 2 to 20 pounds per acre (approximately 0.37 to 3.7 kilograms per hectare) depending on the extent of bird infestation. When the listed compositions are diluted as described above by admixture with powdered mineral material the resulting mixture is applied, again depending on the extent of bird infestation, at a rate of 10 to 50 pounds per acre (approximately 1.8 to 9.2 kilograms per hectare) to the seedline of newly planted plants or to growing vegetable or fruit plants. Corresponding quantities of the listed compositions diluted with an aqueous medium in the ratios stated are similarly applied, as by spraying. When a composition embodying the principles of the present invention is applied, it has been found that birds are repelled for a period of at least six days to about twenty days. However, if either garlic powder or cayenne pepper is applied without the other, its repellant effect lasts about one-third as long as that achieved by compositions of the Examples given above.

Compositions embodying the principles of the present invention are particularly effective in repelling birds of the species *Eremophila alpestris*, commonly known as the horned lark. This bird is particularly well known for causing extensive damage to seeds and sprouts of lettuce and melon plants. The compositions are also effective to repel other birds of varieties commonly referred to as starlings, house finches, and house sparrows and are particularly effective in protecting other produce, such as grapes, peaches, and nectarines against bird damage.

Since the active ingredients of compositions utilized in the practice of the subject inventions are natural, organic materials which are commonly used as spices or flavorings and have been so used for centuries, it is apparent that these compositions are not harmful to the environment or to consumers of produce from plants treated with the compositions. These compositions are applied in a relatively limited quantity and, typically, washed away with the fruit or vegetables are processed in the usual manner. The amount of the composition which is present in or on an article of produce from a plant to which the composition was applied when the plant had just sprouted or which developed from a seed in ground to which the composition was applied, is minimal.

While the compositions of the instant invention are described in terms of particular ingredients, and ranges thereof, it is obvious that modifications and variations in the nature and proportions of the ingredients may be made without departing from the spirit or scope of the invention.

Having described my composition, what I claim as new and desire to secure by Letters Patent is:

1. A method for repelling birds from a crop, the method comprising applying in the vicinity of the crop a composition including finely divided dried garlic constituent and finely divided dried cayenne pepper constituent, the garlic constituent being present in at least about one-fifth to at least about five times the weight of the pepper constituent, dry weight, and the total amount of the garlic and pepper constituents applied being from at least about 0.37 to 3.7 kilograms per hectare.

2. The method of claim 1 wherein the garlic constituent is dried and finely divided garlic bulbs and the pepper constituent is dried and finely divided fruits from plants of the genus Capsicum.

3. The method of claim 2 wherein the pungency of the pepper constituent is in the range of approximately 25,000 to approximately 60,000 Scoville Units.

4. The method of claim 1 wherein the composition includes, as a diluent, finely divided inert mineral material having a weight in the range of about the combined weight of the garlic and the pepper to about fifteen times said combined weight.

5. The method of claim 1 wherein the composition includes, as a diluent, water having a weight in the range of about 40 times the combined weight of the garlic and the pepper to about 400 times said combined weight.

6. A composition for repelling birds from growing crops comprising finely divided, dried garlic and finely divided dried cayenne pepper from pungent fruits of plants from the genus Capsicum, wherein the dried weight of the garlic is from at least about one-fifth of the dried weight of the pepper to at least about five times the dried weight of the pepper.

7. The composition of claim 6 wherein the pungency of the dried pepper is in a range of about 25,000 to 60,000 Scoville Units.

8. The composition of claim 6 wherein the composition further comprises, as a diluent, finely divided inert mineral material selected from the group consisting of dolomite, talc, and phosphate rock and having a weight in the range of at least about the combined weight of the garlic and the pepper to about fifteen times said combined weight.

9. The composition of claim 6 wherein the composition further comprises, as a diluent, water having a weight in the range of about 40 times the combined weight of the garlic and the pepper to about 400 times said combined weight.

* * * * *